US010051867B2

(12) United States Patent
Vernon

(10) Patent No.: US 10,051,867 B2
(45) Date of Patent: Aug. 21, 2018

(54) ANTIMICROBIAL POLYMER CONCENTRATES AND COMPOUNDS

(71) Applicant: PolyOne Corporation, Avon Lake, OH (US)

(72) Inventor: Gary C. Vernon, Sugar Hill, GA (US)

(73) Assignee: PolyOne Corporation, Avon Lake, OH (US)

( * ) Notice: Subject to any disclaimer, the term of this patent is extended or adjusted under 35 U.S.C. 154(b) by 29 days.

(21) Appl. No.: 15/024,881

(22) PCT Filed: Oct. 1, 2014

(86) PCT No.: PCT/US2014/058670
§ 371 (c)(1),
(2) Date: Mar. 25, 2016

(87) PCT Pub. No.: WO2015/051020
PCT Pub. Date: Apr. 9, 2015

(65) Prior Publication Data

US 2016/0235072 A1 Aug. 18, 2016

Related U.S. Application Data

(60) Provisional application No. 61/886,116, filed on Oct. 3, 2013.

(51) Int. Cl.

| | |
|---|---|
| ***C08J 3/22*** | (2006.01) |
| ***C08K 3/32*** | (2006.01) |
| ***A01N 59/16*** | (2006.01) |
| ***C08L 101/00*** | (2006.01) |
| ***C08K 5/09*** | (2006.01) |
| ***C08K 5/46*** | (2006.01) |
| ***C08L 23/12*** | (2006.01) |
| ***C08L 69/00*** | (2006.01) |
| *C08K 3/015* | (2018.01) |

(52) U.S. Cl.
CPC ............. *A01N 59/16* (2013.01); *C08J 3/226* (2013.01); *C08K 3/32* (2013.01); *C08K 5/09* (2013.01); *C08K 5/46* (2013.01); *C08L 23/12* (2013.01); *C08L 69/00* (2013.01); *C08L 101/00* (2013.01); *C08K 3/015* (2018.01); *C08K 2003/328* (2013.01)

(58) Field of Classification Search
CPC .................................. C08J 3/22; C08J 3/226
See application file for complete search history.

(56) References Cited

U.S. PATENT DOCUMENTS

| | | | | |
|---|---|---|---|---|
| 5,929,132 A * | 7/1999 | Hani | A01N 25/04 | 523/122 |
| 6,448,305 B1 * | 9/2002 | Watterson, III | A01N 25/10 | 523/122 |
| 7,491,753 B2 | 2/2009 | Krishnan | | |
| 7,981,946 B2 | 7/2011 | Krishnan | | |
| 8,753,657 B2 | 6/2014 | Kobayashi | | |
| 2007/0139667 A1 | 6/2007 | Russell et al. | | |
| 2008/0142023 A1 * | 6/2008 | Schmid | A01N 25/10 | 128/849 |
| 2010/0264383 A1 * | 10/2010 | Tooley | C08J 3/226 | 252/589 |
| 2014/0170238 A1 * | 6/2014 | Cliff | C09D 5/14 | 424/618 |
| 2014/0329899 A1 | 11/2014 | Nakamura et al. | | |
| 2015/0044449 A1 * | 2/2015 | Foss | C08K 3/22 | 428/221 |
| 2015/0104488 A1 * | 4/2015 | Lackner | C09D 5/14 | 424/409 |

FOREIGN PATENT DOCUMENTS

| | | |
|---|---|---|
| JP | 10-007506 A | 1/1998 |
| KR | 10-1045274 | 6/2011 |
| WO | 2009136185 A1 | 11/2009 |

OTHER PUBLICATIONS

Abstract of WO2012111894 (Thermolon Korea Co., Ltd.).

* cited by examiner

*Primary Examiner* — Brieann R Johnston
(74) *Attorney, Agent, or Firm* — John H. Hornickel

(57) ABSTRACT

Migratory assisting agents are used to improve antimicrobial efficacy of antimicrobial masterbatches, the polymer compounds these antimicrobial masterbatches are let down into, and the articles made therefrom. The migratory assisting agents function by carrying the antimicrobial agents while the migratory assisting agent transfers or "migrates" to the surface of a polymer compound or article formed from the polymer compound. As a result, antimicrobial agents are brought to the surface where there is exposure to bacterial contamination.

19 Claims, No Drawings

ANTIMICROBIAL POLYMER CONCENTRATES AND COMPOUNDS

CLAIM OF PRIORITY

This application claims priority from U.S. Provisional Patent Application Ser. No. 61/886,116 and filed on Oct. 3, 2013, which is incorporated by reference.

FIELD OF THE INVENTION

This invention relates to antimicrobial masterbatches using migratory assisting agents to improve antimicrobial efficacy, the polymer compounds these antimicrobial masterbatches are let down into, and articles made therefrom. Migratory assisting agents function by carrying the antimicrobial agent while the migratory assisting agent transfers or "migrates" to the surface of the polymer compound or article. As a result, antimicrobial agents are brought to the surface where there is exposure to bacterial contamination.

BACKGROUND OF THE INVENTION

Plastic has taken the place of other materials in a variety of industries. Plastic has replaced glass to minimize breakage, reduce weight, and reduce energy consumed in manufacturing and transport. In other industries, plastic has replaced metal to minimize corrosion, reduce weight, and provide color-in-bulk products.

To meet the many applications for plastics, the world in the past seventy years has seen a revolution in material science arising from the combination of a thermoplastic resin and one or more functional additives to provide specific properties to the resin.

Antimicrobial properties have become particularly desirable in plastics used for many applications, including medical equipment, food processing, packaging, healthcare products, consumer and household items.

SUMMARY OF THE INVENTION

Antimicrobial agents can be supplied in the form of thermoplastic concentrates formulated to give the final part antimicrobial properties. These concentrates (also called "masterbatches"), upon blending into the thermoplastic resin, allow the plastic article to kill or inhibit growth of specified types of bacteria that may come into contact with the article. The masterbatches are supplied in a pelletized, non-dusting form tailored to a specific resin system. A typical dilution or "let-down" ratio for a masterbatch ranges from about 100:1 (1%) to about 10:1 (10%), and preferably a range of 25:1 (4%) to about 12.5:1 (8%).

Typical applications for antimicrobial plastic articles include packaging; consumer products, particularly personal care items; medical devices; and any other article or apparatus in which human contact is expected. However, it is often difficult to achieve the desired antimicrobial efficacy in polymer articles, because of regulatory restrictions on the amount of certain antimicrobial ingredients that can be used. For example, the U.S. Environmental Protection Agency limits the maximum weight percent of certain antimicrobial ingredients in the final part to 2% of silver and 0.10% of zinc pyrithione. Moreover, it is particularly challenging under such restrictions to achieve at least a log 2 antimicrobial efficacy for both gram positive (+) and gram negative (−) bacteria.

The present invention solves the problem in the art by enhancing the antimicrobial efficacy of the antimicrobial agents. Unexpectedly, the antimicrobial agent is carried by a migratory assisting agent to the surface of the plastic article (after the plastic article has been formed), where the bacterial performance is required, thus improving both the initial and sustained antimicrobial effectiveness.

One embodiment of the invention is an antimicrobial masterbatch for thermoplastic compounds, comprising a polymer carrier, antimicrobial agent, migratory assisting agent, and optionally other additives. The migratory assisting agent can carry at least some of the antimicrobial agent to a surface of an article formed from the masterbatch.

Another embodiment of the invention is an antimicrobial compound comprising the masterbatch and a base polymer resin.

The antimicrobial compound when extruded into an article can have an improved gram (−) log and gram (+) log according to the JIS Z 2801 test method, compared to the compound without the migratory assisting agent.

Another embodiment of the invention is an antimicrobial compound in the shape of a molded plastic article, an extruded plastic article, a calendered plastic article, a thermoformed plastic article, or a 3D printed plastic article.

Another aspect of the invention is a method of using the antimicrobial compound by shaping the compound into an article designed to have antimicrobial properties. The shaping can be done by extruding, molding, calendering, additive manufacturing, 3D printing or thermoforming.

Other features will become apparent from a description of the embodiments of the invention.

EMBODIMENTS OF THE INVENTION

Polymer Resin

Any polymer resin is a candidate for use in the present invention as a carrier polymer, base polymer resin or both. Preferably, the carrier polymer is selected according to its miscibility in the base polymer resin for improved dispersion of the masterbatch in the compound.

Non-limiting examples of large volume commercial polymer resins include polyolefins, polyamides, polyesters, poly (meth)acrylates, polycarbonates, poly(vinyl halides), polyvinyl alcohols, polynitriles, polyacetals, polyimides, polyarylketones, polyetherketones, polyhydroxyalkanoates, polycaprolactones, polystyrenes, polyurethanes, polysulfones, polyphenylene oxides, polyphenylene sulfides, polyacetates, liquid crystal polymers, fluoropolymers, ionomeric polymers, thermoplastic elastomers, and copolymers of any of them and combinations of any two or more of them.

Published literature exists to identify many commercial species of these categories of thermoplastic resins. Non-limiting examples of specific commercial thermoplastic resins include acrylonitrile butadiene styrene (ABS), polymethyl methacrylate (PMMA), cellulose acetate, cyclic olefin copolymer (COC), ethylene-vinyl acetate (EVA), ethylene vinyl alcohol (EVOH), polytetrafluoroethane (PTFE), ionomers, polyoxymethylene (POM or Acetal), polyacrylonitrile (PAN), polyamide 6, polyamide 6,6, polyamide-imide (PAI), polyaryletherketone (PAEK), polybutadiene (PBD), polybutylene (PB), polybutylene terephthalate (PBT), polycaprolactone (PCL), polychlorotrifluoroethylene (PCTFE), polyethylene terephthalate (PET), polycyclohexylene dimethylene terephthalate (PCT), polycarbonate (PC), polyhydroxybutyrate (PHB), polyethylene (PE), polyetheretherketone (PEEK), polyetherketoneketone (PEKK), polyetherimide (PEI), polyethersulfone (PES), chlorinated polyethylene (CPE), polyimide (PI), polylactic acid (PLA), polymethylpentene (PMP), polyphenylene oxide (PPO), polyphenylene sulfide (PPS), polyphthalamide (PPA), polypropylene (PP), polysulfone (PSU), polytrimethylene terephthalate (PTT), polyurethane (PU), polyvinyl acetate (PVA), polyvinyl chloride (PVC), polyvinylidene chloride (PVDC), and styrene-acrylonitrile (SAN).

Antimicrobial Agents

Any antimicrobial agent known by persons having skill in the art can be used for this invention either individually or in combination of two or more. Among the more commonly recognized antimicrobial agents are chlorhexidine, chlorhexidine gluconate, glutaral, halazone, hexachlorophene, nitrofurazone, nitromersol, povidone-iodine, thimerosol, parabens, hypochlorite salts, clofucarban, clorophene, poloxamer-iodine, phenolics, mafenide acetate, aminacrine hydrochloride, quaternary ammonium salts, oxychlorosene, metabromsalan, merbromin, dibromsalan, glyceryl laurate, sodium and/or zinc pyrithione, (dodecyl) (diethylenediamine) glycine and/or (dodecyl) (aminopropyl) glycine; phenolic compounds, polymeric guanidines, quaternary ammonium salts, polymyxins, bacitracin, circulin, the octapeptins, lysozmye, lysostaphin, cellulytic enzymes generally, vancomycin, ristocetin, actinoidins, avoparcins, tyrocidin A, gramicidin S, polyoxin D, tunicamycin, neomycin, and streptomycin. Preferred for the present invention are antimicrobial metal ions and zinc pyrithone, further described below.

Ionic Metals

Several metals are known in the art to exhibit antimicrobial action in an ionic state, including: silver, copper, zinc, gold, platinum, tin, nickel, and iron. These metal ions are often used in the form of salts, oxides or as a complex.

Preferred for the present invention is the silver-magnesium-aluminum phosphate complex (1.6% silver) Ionpure™ antimicrobial, which is available from Ishizuka Glass Co., Ltd. Ionpure™ antimicrobial is composed of silver ions contained within a transparent glass mesh structure that serves as a carrier. Slowly released at a controlled speed from the glass mesh, the silver ion kills bacteria and inhibits the growth of microorganisms. The silver ions provide an antibacterial efficacy of over 99.9% against a wide spectrum of bacteria species.

Also preferred for the present invention are Intercide ZNP™ microbiocides based on zinc pyrithione, which has the molecular formula $C_{10}H_8N_2O_2S_2Zn$. The pyrithione ligands of the zinc pyrithione are chelated to $Zn^{2+}$ via oxygen and sulfur centers. Zinc pyrithione is effective against many pathogens from the *Streptococcus* and *Staphylococcus* genera.

Migratory Assisting Agent

Any additive that migrates (i.e. "blooms") to the surface of a polymer can be used as a migratory assisting agent for the present invention. The migratory assisting agent functions by carrying the antimicrobial agent to the surface of the plastic article. The migratory assisting agent need not have any antimicrobial efficacy on its own. Examples of migratory assisting agents are antiblock, slip, surfactant blend and antistatic additives and polymeric lubricants (e.g. siloxanes).

Organic antiblocks additives, include for example, bisamides, secondary amide, primary amide, organic stearate, and metallic stearates. Typical inorganic antiblock additives are, for example, natural and synthetic silica (silicon dioxide, $SiO_2$), talc (magnesium silicate), calcium carbonate ($CaCO_3$), ceramic spheres (alumina-silicate ceramic), kaolin/clay (aluminum silicate), and mica (aluminum potassium silicate).

Typical slip additives are, for example, oleamide, erucamide, stearamide, behenamide, oleyl palmitamide, stearyl erucamide, ethylene bis-oleamide, and N,N'-Ethylene Bis (Stearamide) (EBS), polyol partial esters; and hydrogenated soybean oil.

Colorant

A colorant can be a pigment, a dye, a combination of pigments, a combination of dyes, a combination of pigments and dye, a combination of pigment and dyes, or a combination of pigments and dyes. The choice of colorants depends on the ultimate color desired by the designer for the plastic article.

The science of color is well known to those skilled in the art. Without undue experimentation, one can use color matching techniques to identify a particular location in spherical color space. For example, one skilled in the art can use the teachings of PCT Patent Publication WO/2004/095319 to digitally map color space using specific polymer carriers and colorants as raw material ingredients. Alternatively, one can make small samples called plaques for visual review.

Colorants are commercially available from a number of sources well known to those skilled in the art. Commercially available pigments are well known to those skilled in the art and include organic and inorganic colorant chemistries. Commercially available dyes are well known to those skilled in the art and include all organic chemistries. Commercial sources for pigments and dyes include multinational companies such as BASF, Bayer, Color-Chem International, Sun Chemical, and Zhuhai Skyhigh Chemicals.

Optional Functional Additives

Optionally, conventional plastics additives can be added to either the antimicrobial masterbatch or the let-down polymer compound of the invention, in an amount that is sufficient to obtain a desired processing or performance property for the compound. The amount should not be wasteful of the additive nor detrimental to the processing or performance of the compound. Those skilled in the art of thermoplastics compounding, without undue experimentation but with reference to such treatises as *Plastics Additives Database* (2004) from Plastics Design Library (elsevier.com website), can select from many different types of additives for inclusion into the compounds of the present invention.

Non-limiting examples of optional additives include heat stabilizers, char formers, adhesion promoters; biocides; anti-fogging agents; anti-static agents; anti-oxidants; bonding, blowing and foaming agents; dispersants; fillers and extenders; smoke suppressants; impact modifiers; initiators; lubricants; micas; pigments, colorants and dyes; plasticizers; processing aids; release agents; silanes, titanates and zirconates; slip agents, anti-blocking agents; stearates; ultraviolet light absorbers; viscosity regulators; waxes; catalyst deactivators, and combinations of them.

Generally, minor amounts of such additives provide improvement of performance to the masterbatch or polymer compound during processing with the other ingredients in the polymer resin or in performance of the polymeric molded article after manufacturing. One skilled in the art without undue experimentation can determine the appropriate concentration.

Table 1 shows acceptable, desirable, and preferable ranges of ingredients useful in the masterbatch of the present invention, all expressed in weight percent (wt. %) of the masterbatch. The masterbatch can comprise, consist essentially of, or consist of these ingredients.

TABLE 1

| Ingredient (Wt. %) | Acceptable Range | Desirable Range | Preferred Range |
|---|---|---|---|
| Polymer Carrier | 15-99.99 | 20-99.5 | 60-98 |
| Antimicrobial Agents | 0.01-5.0 | 0.1-5 | 1.0-2.2 |
| Migratory Assisting Agents | 0.01-5.0 | 0.01-1.0 | 0.02-0.24 |
| Colorant | 0-80 | 0-75 | 0-65 |
| Optional Functional Additives | 0-65 | 0-55 | 0-50 |

The masterbatch can be "let-down" into a base polymer resin according to a ratio of base polymer resin to masterbatch ranging from about 100:1 (1%) to about 10:1 (10%), and preferably 25:1 (4%) to about 12.5:1 (8%).

Processing of the Masterbatch

One can prepare the masterbatch using continuous or batch techniques, using extruders or mixers, respectively. The mixing equipment can be any suitable equipment already used in the art of mixing highly concentrated solids. For example, such equipment includes high speed Henschel mixers, ribbon blenders, shakers, extruders and the like.

Mixing in a continuous process typically occurs in an extruder that is elevated to a temperature that is sufficient to melt the polymer carrier with addition either at the head of the extruder or downstream in the extruder of the solid ingredient additives. Extruder speeds can range from about 50 to about 500 revolutions per minute (rpm), and preferably from about 100 to about 300 rpm. Typically, the output from the extruder is pelletized for later extrusion, molding, or calendering into polymeric articles.

Alternatively, mixing in a batch process typically occurs in a Banbury or other batch mixer that is also elevated to a temperature that is sufficient to melt the polymer matrix to permit addition of the solid ingredient additives. The mixing speeds range from 60 to 1000 rpm. Also, the output from the mixer is chopped into smaller sizes for later extrusion, molding, or calendering into polymeric articles.

The concentration of antimicrobial agent into the polymer carrier is significant because of the relative cost of the antimicrobial agent ingredient(s), and the need for the antimicrobial agent to consistently and precisely mix and disperse into the polymer carrier and then to consistently and precisely dilute into the base polymer resin and other compound ingredients during "let-down". Let-down ratios depend on the antimicrobial activity required for the final article.

Subsequent Processing of the Compound and Polymeric Article

Let-down of the masterbatch of the invention into a polymer compound may be done during subsequent steps of reshaping by extrusion, molding, or calendering. Processing begins with melt-mixing the masterbatch with the base polymer resin followed by reshaping by extrusion, molding, or calendering, followed by natural or accelerated cooling to form the final plastic article desired.

In the case of molding, particularly injection molding, the reshaping step includes pressurized injecting, holding, and cooling steps before the plastic article is ejected, the cycle of which the time is being measured to determine cycle time. More specifically, the reshaping step comprises four substeps of (1) injecting the compound into a mold; (2) holding the compound in the mold to form the plastic article in the shape of the mold; (3) cooling the plastic article to permit the plastic article to be released from the mold while retaining shape of the mold; and (4) ejecting the final plastic article.

Subsequent extrusion or molding techniques are well known to those skilled in the art of thermoplastics polymer engineering. Without undue experimentation but with such references as "Extrusion, The Definitive Processing Guide and Handbook"; "Handbook of Molded Part Shrinkage and Warpage"; "Specialized Molding Techniques"; "Rotational Molding Technology"; and "Handbook of Mold, Tool and Die Repair Welding", all published by Plastics Design Library (williamandrew.com), one can make articles of any conceivable shape and appearance using compounds of the present invention.

USEFULNESS OF THE INVENTION

The antimicrobial masterbatches of the present invention can be let-down into polymers resins, with other ingredients, to make molded, calendered, extruded, thermoformed, or 3D printed antimicrobial articles.

In the present invention, the migratory assisting agent is added for the purpose of migrating the antimicrobial agent to the surface of the polymer, and not for the known performance characteristics of that migratory assisting agent. Therefore, the migratory assisting agent can oftentimes be used at lower levels than a person having ordinary skill in the art would use the migratory assisting agent if trying to exploit the additive for its known purpose, such as using an anti-static agent for its anti-static properties or a slip agent for its slip properties. Similarly, due to the synergism between the migratory assisting agent and the antimicrobial agent, less of the antimicrobial agent is needed to meet the gram (−) log and gram (+) log according to JIS Z 2801 that is required for an application.

Antimicrobial characteristics are desirable for articles used in many applications, including; communication equipment (stationary, mobile, and handheld, including telephones, headsets, handsets, intercoms, earphones, and microphones and other input/output devices); medical and healthcare products (wheelchairs, beds, testing equipment, packaging, gloves, medical equipment, catheters, protective covers, and medical tubing); household items (including shower curtains, containers, handles, sponges); and packaging (food and beverage, cosmetic, detergents and cleaners, personal care, pharmaceutical and wellness).

In many applications a gram (+) and gram (−) log reduction of at least 2 is desired. For certain applications a gram (+) and gram (−) log reduction of at least 3 is preferred.

The JIS Z 2801 method is designed to quantitatively test the ability of plastics to inhibit the growth of microorganisms or kill them, over a 24 hour period of contact. Control and test surfaces are inoculated with microorganisms, in triplicate, and then the microbial inoculum is covered with a thin, sterile film. Covering the inoculum spreads it, prevents it from evaporating, and ensures close contact with the antimicrobial surface. Microbial concentrations are determined at "time zero" by elution followed by dilution and plating. A control is run to verify that the neutralization/elution method effectively neutralizes the antimicrobial agent in the antimicrobial surface being tested. Inoculated, covered control and antimicrobial test surfaces are allowed to incubate undisturbed in a humid environment for 24 hours.

After incubation, microbial concentrations are determined. The antimicrobial activity is calculated based on the reduction of microorganisms relative to initial concentrations as calibrated by the control surface. The species of bacteria used for this test are *Staphylococcus aureus* (gram positive (+)) and *Escherichia coli* (gram negative (−)).

EXAMPLES

Table 2 shows the ingredients used for the Comparative Examples and the Examples.

TABLE 2

| Brand | Ingredient Name | Purpose | Source (Company and Location) |
|---|---|---|---|
| Ionpure WPA | 1.6% silver from a silver-magnesium-aluminum phosphate complex | Antimicrobial | Ishizuka Glass Co., Ltd. |
| Intercide ZNP | Zinc pyrithione powder | Antimicrobial | Arch Chemicals, Inc. |
| Pationic ® 1052 | glycerol mono stearate with a 52% minimum alpha-monoester content | Antistatic agent | Patco Additives |
| Chemstat ® 1900 | Surfactant Blend-polymer | Antistatic agent | PCC Chemax Products |
| PLAs-Chek 775 | Epoxidized soybean oil | Process Aid | Ferro Corporation |
| Songnox 1010 PW | Phenolic antioxidant | Stabilizer | BASF Plastic Additives |
| Irgafos ® 168 | Trisarylphosphite | Stabilizer | Ciba Specialty Chemicals Corporation |
| Celanex ® Co-Spec PBT IV | Polybutylene Terephalate | Polymer carrier | Ticona Engineering Polymers |
| SAN Polymer 21 | Styrene acrylonitrile | Polymer carrier | INEOS |
| LLDPE Polymer | Linear low density polyethylene | Polymer carrier | Dow Chemical Company |
| PP Polymer (H) 32 | Polypropylene | Polymer carrier | Flint Hills |
| ABS 6MI | Acrylonitrile Butadiene Styrene | Polymer carrier | INEOS |
| Santoprene ™ 8221-60 | Thermoplastic elastomer | Base Resin | ExxonMobil Chemical |
| Triax ® 1120 ABS | ABS (Acrylonitrile Butadiene Styrene)/Nylon 6 alloy | Base Resin | INEOS |
| Valox ™ 357 | Polycarbonate/ PBT (polybutylene terephthalate) alloy | Base Resin | Sabic Innovative Plastics |
| FHR Polypropylene P4G3Z-039 | Polypropylene Homopolymer | Base Resin | Flint Hills |
| Polycarbonate 243R | Polycarbonate | Base Resin | Sabic Innovative Plastics |

Table 5 shows the formulations of the Masterbatches and Table 6 shows the formulations of the Masterbatches let-down into the antimicrobial polymer compounds of the Comparative Examples A-D and Examples 1-8.

Processing Conditions

The Masterbatches were made using a Henschel brand mixer (high intensity mixer) operating at 1000 rpm and at 85° C. for one minute to thoroughly mix the ingredients. Then, the mixture was then extruded in a co-rotating screw extruder at about 180° C.-285° C. according to Table 3 below, and pelletized.

TABLE 3

| Extruder Conditions All Comparative Examples and Examples | |
|---|---|
| Extruder Type | Coperian/25 mm size twin screw extruder |
| Zone 1 (set) | 150° C. |
| Zone 2 (set) | 180° C. |
| Zone 3 (set) | 185° C. |
| Zone 4 (set) | 190° C. |
| Zone 5 (set) | 190° C. |
| Zone 6 (set) | 190° C. |
| Zone 7(set) | 190° C. |
| Zone 8(set) | 195° C. |
| Zone 9 (set) | 200° C. |
| Die | 200° C. |
| RPM | 500 |

To prepare Comparative Examples A-D and Examples 1-8, a percentage of each Masterbatch was let down into a base resin. The Masterbatch was metered into the base resin in a co-rotating screw extruder through a side feeder to maintain the integrity of the material before pelletizing according to the conditions in Table 4.

TABLE 4

| Extruder Conditions All Comparative Examples and Examples | |
|---|---|
| Extruder Type | Coperian/25 mm size twin screw extruder |
| Order of Addition | Masterbatches were side fed downstream |
| Zone 1 (set) | 150° C. |
| Zone 2 (set) | 180° C. |
| Zone 3 (set) | 185° C. |
| Zone 4 (set) | 190° C. |
| Zone 5 (set) | 190° C. |
| Zone 6 (set) | 190° C. |
| Zone 7(set) | 190° C. |
| Zone 8(set) | 195° C. |
| Zone 9 (set) | 200° C. |
| Die | 200° C. |
| RPM | 500 |

The pelletized polymer compound was then injection molded to form 50 mil plaques. The examples were tested for their gram (−) and gram (+) log reduction using the JIS Z 2801 test method described earlier for antimicrobial activity of plastics. The test results are shown in Table 6.

TABLE 5

| Masterbatch Formulations | | | | | | | | | |
|---|---|---|---|---|---|---|---|---|---|
| | Masterbatch Example | | | | | | | | |
| Ingredient | I | II | III | IV | V | VI | VII | VIII | IX |
| Ionpure WPA | 42.50 | 21.25 | 42.50 | 42.50 | 25.00 | 25.00 | 50.00 | 50.00 | 50.00 |
| Intercide ZNP Powder | 2.50 | 1.25 | 2.50 | 2.50 | 1.25 | 1.25 | 2.50 | 2.50 | 2.50 |
| Pationic 1052 | | | | | | | | 1.00 | 1.00 |

TABLE 5-continued

| Masterbatch Formulations | | | | | | | | | |
|---|---|---|---|---|---|---|---|---|---|
| | Masterbatch Example | | | | | | | | |
| Ingredient | I | II | III | IV | V | VI | VII | VIII | IX |
| Chemstat 1900 | | | | | 3.00 | 3.00 | 1.00 | | |
| PLAs-Chek 775 | 1.00 | 1.00 | 1.00 | 1.00 | | | 1.00 | 1.00 | 1.00 |
| Songnox 1010 PW | 0.20 | 0.20 | 0.20 | 0.20 | 0.20 | 0.20 | 0.20 | 0.20 | 0.20 |
| Irgafos 168 | | | | | | | 0.15 | | |
| Co-Spec PBT IV | | | 53.80 | | 70.55 | | | | |
| SAN Polymer 21 | | 76.30 | | | | | 45.15 | | |
| LLDPE Polymer | 53.80 | | | | | | | 45.30 | |
| PP Polymer (H) 32 | | | | 53.80 | | | | | 45.30 |
| ABS 6MI | | | | | | 70.55 | | | |
| Total | 100.00 | 100.00 | 100.00 | 100.00 | 100.00 | 100.00 | 100.00 | 100.00 | 100.00 |

TABLE 6

| Compound Formulations and Antimicrobial Efficacy | | | | | | | | | | | | |
|---|---|---|---|---|---|---|---|---|---|---|---|---|
| Compound Example | A | B | C | D | 1 | 2 | 3 | 4 | 5 | 6 | 7 | 8 |
| Ingredient | | | | | | | | | | | | |
| Ionpure WPA | 1.70 | 1.70 | 1.70 | 1.70 | 2.00 | 1.00 | 1.00 | 2.00 | 1.00 | 2.00 | 1.00 | 2.00 |
| Intercide ZNP | 0.10 | 0.10 | 0.10 | 0.10 | 0.10 | 0.05 | 0.05 | 0.10 | 0.05 | 0.10 | 0.05 | 0.10 |
| Patiomc 1052 | | | | | | | 0.02 | 0.04 | 0.02 | 0.04 | 0.02 | 0.04 |
| Chemstat 1900 | | | | | 0.24 | 0.12 | | | | | | |
| PLAs-Chek 775 | 0.04 | 0.08 | 0.04 | 0.04 | | | 0.02 | 0.04 | 0.02 | 0.04 | 0.02 | 0.04 |
| Songnox 1010 PW | 0.01 | 0.02 | 0.01 | 0.01 | 0.02 | 0.01 | 0.00 | 0.01 | 0.00 | 0.01 | 0.00 | 0.01 |
| Irgafos 168 | | | | | | | | | | | 0.00 | 0.01 |
| Co-Spec PBT IV | | | 2.15 | | 5.64 | | | | | | | |
| SAN Polymer 21 | | 6.10 | | | | | | | | | 0.91 | 1.81 |
| LLDPE Polymer | 2.15 | | | | | | 0.91 | 1.81 | | | | |
| PP Polymer (H) 32 | | | | 2.15 | | | | | 0.91 | 1.81 | | |
| ABS 6MI | | | | | | 2.82 | | | | | | |
| 8221-60 Santoprene | 96.00 | | | | | | 98.00 | 96.00 | | | | |
| 1120 Triax | | 92.00 | | | | 96.00 | | | | | | |
| Valox 357 | | | 96.00 | | 92.00 | | | | | | | |
| FHR Polypropylene P4G3Z-039 | | | | 96.00 | | | | | 98.00 | 96.00 | | |
| Polycarbonate 243R | | | | | | | | | | | 98.00 | 96.00 |
| Total | 100.00 | 100.00 | 100.00 | 100.00 | 100.00 | 100.00 | 100.00 | 100.00 | 100.00 | 100.00 | 100.00 | 100.00 |
| % let-down for final product | 4.00 | 8.00 | 4.00 | 4.00 | 8.00 | 4.00 | 2.00 | 4.00 | 2.00 | 4.00 | 2.00 | 4.00 |
| Masterbatch let-down | I | II | III | IV | V | VI | VIII | VIII | IX | IX | VII | VII |
| Test Results | | | | | | | | | | | | |
| Gram (−) log reduction # *Escherichia coli* | 0.16 | 1.23 | 0.00 | 2.00 | 5.20 | 5.20 | 4.80 | 5.00 | 4.80 | 4.80 | 5.20 | 5.20 |
| Gram (+) log reduction # *Staphylococcus aureus* | 3.92 | 0.58 | 1.28 | 2.93 | 5.20 | 5.20 | 3.90 | 4.00 | 3.90 | 3.90 | 4.20 | 4.20 |

Comparative Examples A-D served as controls to demonstrate the effectiveness of the antimicrobial agents (a combination of silver-magnesium-aluminum phosphate complex and zinc pyrithione powder), without a migratory assisting agent, in different polymer resins: thermoplastic elastomers, styrene-nylon alloy, polycarbonate/PBT alloy, and polyolefins respectively. Comparative Examples A-D were prepared by letting down Masterbatches I-IV, which excluded any type of migratory additive, into the selected base resin.

When tested for antimicrobial efficacy, Comparative Examples B and C failed to reach the minimum desirable log 2.0 for either the gram negative (−) or gram positive (+) bacteria tested. Comparative Example A failed to reach the minimum desirable log 2.0 for the gram positive (+) bacteria tested. Only Comparative Example D achieved at least the minimum desirable log 2.0 for the gram negative (−) or gram positive (+) bacteria tested.

Examples 1-8 added a migratory assisting agent to the Masterbatches V-IX. Unexpectedly, Examples 1-8 all demonstrated improved antimicrobial efficacy compared to the corresponding Comparative Examples, as discussed below.

Example 1 and Comparative Example C showed the use of antimicrobial agents, with and without a migratory assisting agent respectively, in a polycarbonate/PBT alloy. Although Example 1 used 0.3% more of the antimicrobial agents, this increased amount does not correspond to the surprising increase in antimicrobial activity, particularly from zero for gram (−) bacteria in Comparative Example C to a 5.2 log antimicrobial activity for gram (−) bacteria in Example 1. In addition, Examples 7 and 8 in polycarbonate resin demonstrated a similar surprising increase in antimicrobial activity, and with Example 7 using less of the antimicrobial agents compared to Comparative Example C.

Example 2 demonstrates the use of a migratory assisting agent with less antimicrobial agent in a styrene-nylon alloy. Compared to the control, Comparative Example B, Example 2 has significantly increased antimicrobial activity, even though it uses almost half of the amount of antimicrobial agent. Finally Examples 3 and 4, which correspond to Comparative Example A for thermoplastic elastomers; and Examples 5 and 6, which correspond to Comparative Example D for polyolefins, show a significant increase in the antimicrobial activity with the use of a migratory assisting agent, even when using less of the antimicrobial agents in Examples 3 and 5.

Therefore, the migratory assisting agent permits antimicrobial surface protection of plastic articles more efficiently given a specific concentration of antimicrobial agent. That unexpected result allows for either the same amount of antimicrobial agent in the compound with increased surface efficacy or a reduced amount of antimicrobial agent in the compound with the same surface efficacy. The amount of antimicrobial agents can be less than about 5% or preferably less than about 2.5% and still achieve a surface efficacy for gram (−) and gram (+) bacteria of at least log 2, and preferably at least about log 4 according to the JIS Z 2801 test method. The amount of improvement in efficacy of the present invention, compared to the compound without the migratory assisting agent, can range from an increase of at least 33% of either the gram (−) log or gram (+) log to as much as a 3025% increase of the gram (−) log all other factors being equal.

The invention is not limited to the above embodiments. The claims follow.

What is claimed is:

1. An antimicrobial masterbatch for thermoplastic compounds, comprising:

(a) a polymer carrier (b) antimicrobial agent of a combination of silver-magnesium-aluminum phosphate complex and zinc pyrithione, (c) from one to three weight percent of the masterbatch of a migratory assisting agent comprising a stearate, and (d) optionally other additives.

2. The masterbatch of claim 1, wherein the migratory assisting agent having anti-static properties comprises a glycerol mono stearate.

3. The masterbatch of claim 1, wherein the migratory assisting agent will carry at least some of the antimicrobial agent to a surface of an article formed from the masterbatch.

4. The masterbatch of claim 1, wherein the polymer carrier is selected from the group consisting of polyolefins, polyamides, polyesters, poly (meth)acrylates, polycarbonates, poly(vinyl halides), polyvinyl alcohols, polynitriles, polyacetals, polyimides, polyarylketones, polyetherketones, polyhydroxyalkanoates, polycaprolactones, polystyrenes, polyurethanes, polysulfones, polyphenylene oxides, polyphenylene sulfides, polyacetates, liquid crystal polymers, fluoropolymers, ionomeric polymers, thermoplastic elastomers, and copolymers of any of them and combinations of any two or more of them.

5. The masterbatch of claim 1, wherein other additives are selected from the group consisting of anti-blocking agents; adhesion promoters; fungicides; mildewcides; anti-fogging agents; bonding, blowing and foaming agents; dispersants; fillers and extenders; fire and flame retardants and smoke suppressants; impact modifiers; initiators; lubricants; micas; pigments, colorants and dyes; plasticizers; processing aids; other slip or release agents; other anti-static agents; silanes, titanates and zirconates; stabilizers; stearates; ultraviolet light absorbers; viscosity regulators; waxes; and combinations of them.

6. An antimicrobial compound comprising the masterbatch of claim 1 and a base polymer resin.

7. The antimicrobial compound of claim 6, wherein the base polymer resin is selected from the group consisting of polyolefins, polyamides, polyesters, poly (meth)acrylates, polycarbonates, poly(vinyl halides), polyvinyl alcohols, polynitriles, polyacetals, polyimides, polyarylketones, polyetherketones, polyhydroxyalkanoates, polycaprolactones, polystyrenes, polyurethanes, polysulfones, polyphenylene oxides, polyphenylene sulfides, polyacetates, liquid crystal polymers, fluoropolymers, ionomeric polymers, thermoplastic elastomers, and copolymers of any of them and combinations of any two or more of them.

8. The antimicrobial compound of claim 6, wherein the compound when extruded into an article has an improved gram (−) log and gram (+) log according to the JIS Z 2801 test method, compared to the compound without the migratory assisting agent.

9. The antimicrobial compound of claim 6, further comprising additives selected from the group consisting of anti-blocking agents; adhesion promoters; fungicides; mildewcides; anti-fogging agents; bonding, blowing and foaming agents; dispersants; fillers and extenders; fire and flame retardants and smoke suppressants; impact modifiers; initiators; lubricants; micas; pigments, colorants and dyes; plasticizers; processing aids; other slip or release agents; other anti-static agents; silanes, titanates and zirconates; stabilizers; stearates; ultraviolet light absorbers; viscosity regulators; waxes; and combinations of them.

10. The antimicrobial compound of claim 6, wherein the amount of masterbatch let down into base resin ranges from 1% to 10% of the weight percent of the compound.

11. The antimicrobial compound of claim 6, in the shape of a molded plastic article, an extruded plastic article, a calendered plastic article, a thermoformed plastic article, or a 3D printed plastic article.

12. A molded article made from the antimicrobial compound of claim 6.

13. An extruded article made from the antimicrobial compound of claim 6.

14. A calendered article made from antimicrobial compound of claim 6.

15. A thermoformed article made from the antimicrobial compound of claim 6.

16. The masterbatch of claim 2, wherein the migratory assisting agent will carry at least some of the antimicrobial agent to a surface of an article formed from the masterbatch.

17. An antimicrobial compound comprising the masterbatch of claim 2 and a base polymer resin.

18. The antimicrobial compound of claim 17, wherein the compound when extruded into an article has an improved gram (−) log and gram (+) log according to the JIS Z 2801 test method, compared to the compound without the migratory assisting agent.

19. The antimicrobial compound of claim 18, wherein the amount of masterbatch let down into base resin ranges from 1% to 10% of the weight percent of the compound.

* * * * *